United States Patent [19]

Arai et al.

[11] Patent Number: 4,579,963

[45] Date of Patent: Apr. 1, 1986

[54] ORGANOSILICON COMPOUND AND A ROOM TEMPERATURE CURABLE ORGANOPOLYSILOXANE COMPOSITION FORMULATED THEREWITH

[75] Inventors: Masatoshi Arai; Koji Futatsumori; Takeo Inoue; Shinichi Sato, all of Gunma, Japan

[73] Assignee: Shin-Etsu Chemical Co., Ltd., Tokyo, Japan

[21] Appl. No.: 710,128

[22] Filed: Mar. 11, 1985

[30] Foreign Application Priority Data

Mar. 12, 1984 [JP] Japan .................................. 59-46926
Mar. 13, 1984 [JP] Japan .................................. 59-47795

[51] Int. Cl.$^4$ ........................... C07F 7/04; C07F 7/08; C07F 7/10; C07F 7/18
[52] U.S. Cl. .................... 556/423; 556/446; 556/449; 556/479; 528/34
[58] Field of Search ............... 556/479, 446, 449, 423

[56] References Cited

U.S. PATENT DOCUMENTS 3,907,850 9/1975 Capka et al. .................... 556/479 X Primary Examiner—Paul F. Shaver
Attorney, Agent, or Firm—Toren, McGeady, Stanger, Goldberg & Kiel

[57] ABSTRACT

The invention provides a novel class of organosilicon compounds useful as a curing agent in a room temperature curable organopolysiloxane composition, which is represented by the general structural formula $$R_2CH-CR=C(OR)-O-Si(R^1)_{3-m}(O-CR=CH-R)_m,$$

in which each R is a hydrogen atom or a substituted or unsubstituted monovalent hydrocarbon group independently from the others, $R^1$, if any, is a substituted or unsubstituted monovalent hydrocarbon group and the suffix m is 2 or 3. The compound can readily be synthesized by the reaction of an α,β-unsaturated ester compound represented by the general formula $$R_2C=CR-CO-OR,$$

and an alkenyloxy-containing silane compound represented by the general formula $$HSi(R^1)_{3-m}(O-CR=CH-R)_m,$$

in which $R^1$, R and m each have the meaning as defined above, in the presence of a rhodium compound as a catalyst. The room temperature curable composition is formulated with (a) 100 parts by weight of a diorganopolysiloxane terminated at both molecular chain ends each with a silanolic hydroxy group and having a viscosity in the range from 100 to 1,000,000 centistokes at 25° C.; (b) from 2 to 40 parts by weight of the novel organosilicon compound and (c) from 0.01 to 10 parts by weight of a curing accelerator which is preferably a 2-guanidino-containing organosilicon compound.

9 Claims, 5 Drawing Figures

ORGANOSILICON COMPOUND AND A ROOM TEMPERATURE CURABLE ORGANOPOLYSILOXANE COMPOSITION FORMULATED THEREWITH

BACKGROUND OF THE INVENTION

The present invention relates to a novel organosilicon compound and a method for the preparation thereof as well as a room temperature curable organopolysiloxane composition, which is referred to as a RTV silicone composition hereinbelow, formulated with the organosilicon compound as a curing agent.

There are known several different types of RTV silicone compositions capable of giving a cured product having rubber-like elasticity according to the mechanism of the reaction for the crosslink formation in which different kinds of condensation products are liberated in the course of curing including acetic acid, an amine compound, an oxime compound, an alcohol compound and the like. The toxicity and/or corrosiveness as well as the offensive odor of the condensation products such as the acetic acid, amine and oxime compounds present a serious problem in the practical application of the RTV silicone compositions when they are cured with liberation of these noxious gases. The compositions curable by the dealcoholation condensation are disadvantageous in the relatively low stability of a ready-mixed composition in storage.

Therefore, an improvement has been recently proposed according to which the curing agent formulated in the RTV silicone composition is an alkenyloxy-containing organosilicon compound and the condensation product liberated in the course of the curing reaction thereof is a relatively innoxious ketone compound. A problem in such a deketonation-type composition is the extremely high cost of the alkenyloxy-containing organosilicon compound due to the very lengthy time taken for the synthesis of the compound and the low yield of the desired reaction product, for example, in the range of 50 to 60%.

Accordingly, the inventors have conducted extensive investigations to seek a novel organosilicon compound usable as a curing agent in a RTV silicone composition free from the above described problems and disadvantages in the prior art curing agents or compositions.

SUMMARY OF THE INVENTION

It is therefore a primary object of the invention to provide a novel RTV silicone composition capable of giving a cured product having excellent rubber-like mechanical properties without the above described problems and disadvantages in the prior art RTV silicone compositions.

A secondary object of the invention is accordingly to provide an organosilicon compound which is useful as a curing agent when formulated in an organopolysiloxane mixture to give a RTV silicone composition which can be cured without the problems and disadvantages as mentioned above.

A further object of the invention is to provide a method for the preparation of the above mentioned organosilicon compound useful as a curing agent in a RTV silicone composition.

Thus, the organosilicon compound useful as a curing agent of a RTV silicone composition discovered as a result of the extensive investigations undertaken by the inventors is a novel organosilane compound not described in any prior art publications and represented by the general structural formula $$R_2CH-CR=C(OR)-O-Si(R^1)_{3-m}(O-CR=CH-R)_m, \quad (I)$$

in which each R is a hydrogen atom or a substituted or unsubstituted monovalent hydrocarbon group independently from the others, $R^1$, if any, is a substituted or unsubstituted monovalent hydrocarbon group and the suffix m is 2 or 3.

The above defined novel organosilane compound can be readily synthesized by the addition reaction between an α,β-unsaturated ester compound represented by the general formula $$R_2C=CR-CO-OR, \quad (II)$$

in which each R has the same meaning as defined above, and an alkenyloxy-containing silane compound represented by the general formula $$HSi(R^1)_{3-m}(O-CR=CH-R)_m, \quad (III)$$

in which R, $R^1$, if any, and m each have the same meaning as defined above, in the presence of a rhodium compound as a catalyst.

Further, the RTV silicone composition of the invention formulated with the above defined novel organosilicon compound as a curing agent comprises:

(a) 100 parts by weight of a diorganopolysiloxane terminated at both molecular chain ends each with a silanolic hydroxy group and having a viscosity in the range from 100 to 1,000,000 centistokes at 25° C.;

(b) from 2 to 40 parts by weight of an organosilicon compound represented by the above described general formula (I); and (c) from 0.01 to 10 parts by weight of a curing accelerator which is preferably an organosilicon compound having, in a molecule, at least one 2-guanidino group of the formula $$(R^2_2N-)_2C=N-, \quad (IV)$$

in which each $R^2$ is a monovalent hydrocarbon group having from 1 to 8 carbon atoms.

DETAILED DESCRIPTION OF THE PREFERRED EMBODIMENTS

Figure 1:
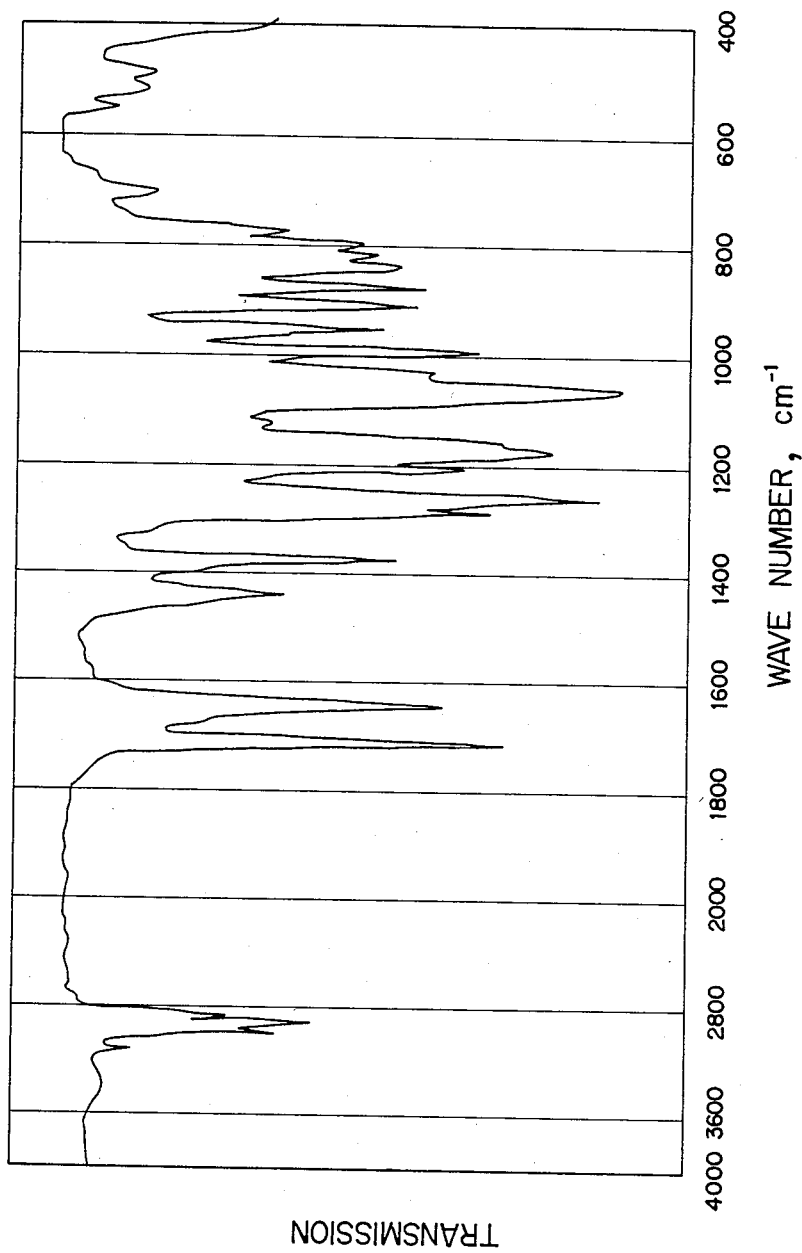
FIGS. 1 to 5 each illustrate an infrared absorption spectrum of the organosilicon compound prepared in Examples 1 to 5, respectively.
Figure 2:
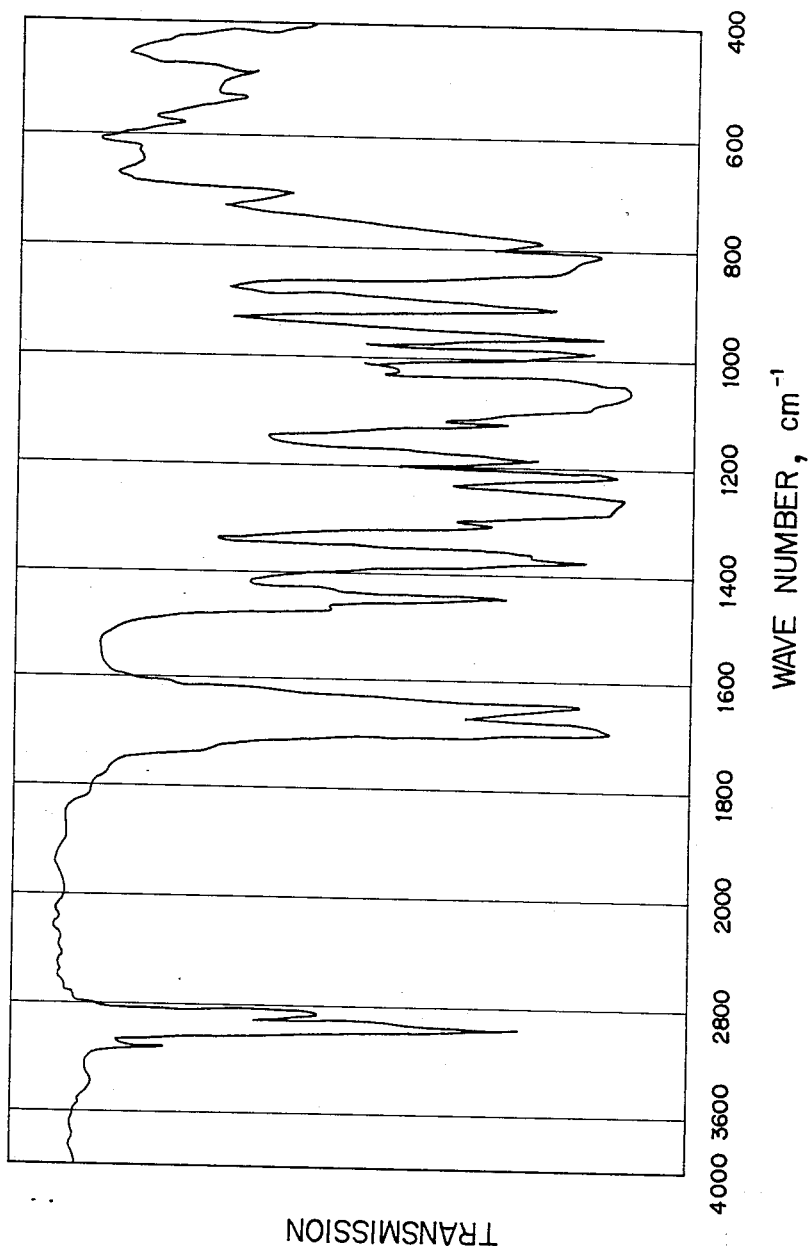
Figure 3:
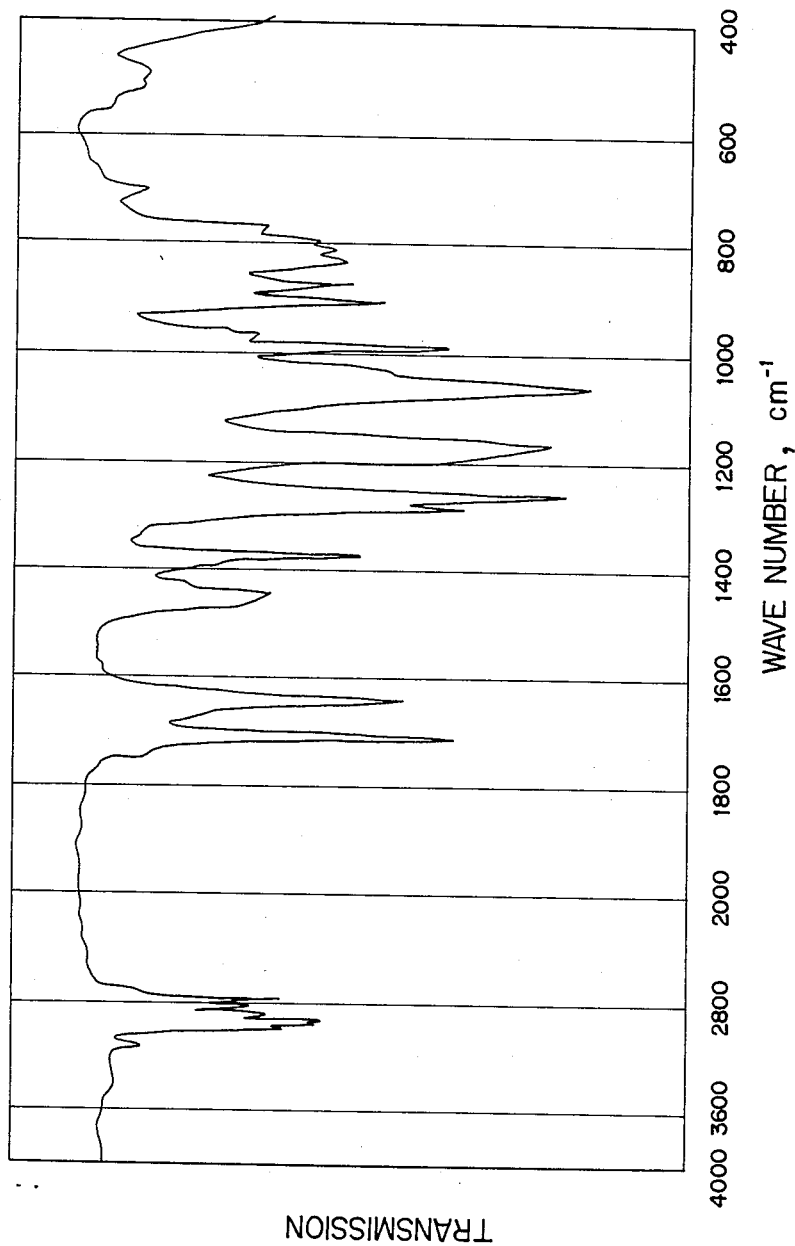
Figure 4:
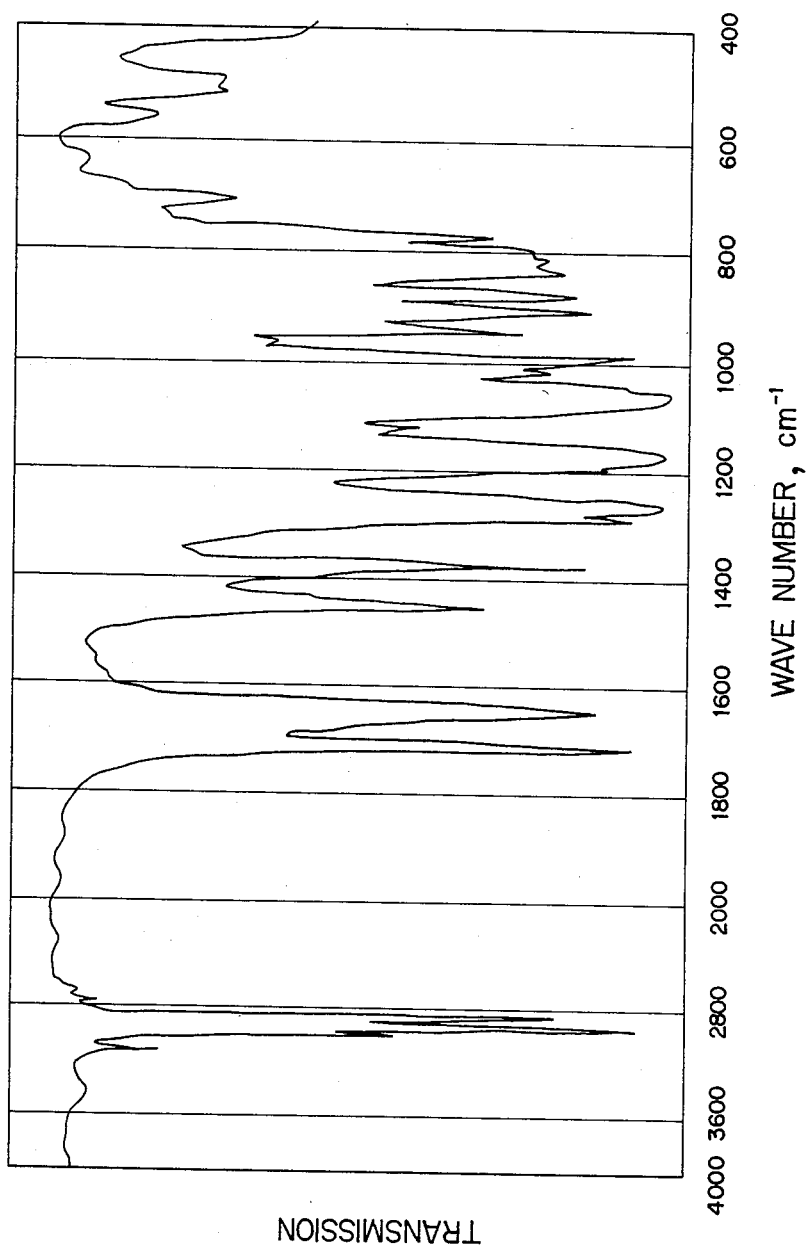
Figure 5:
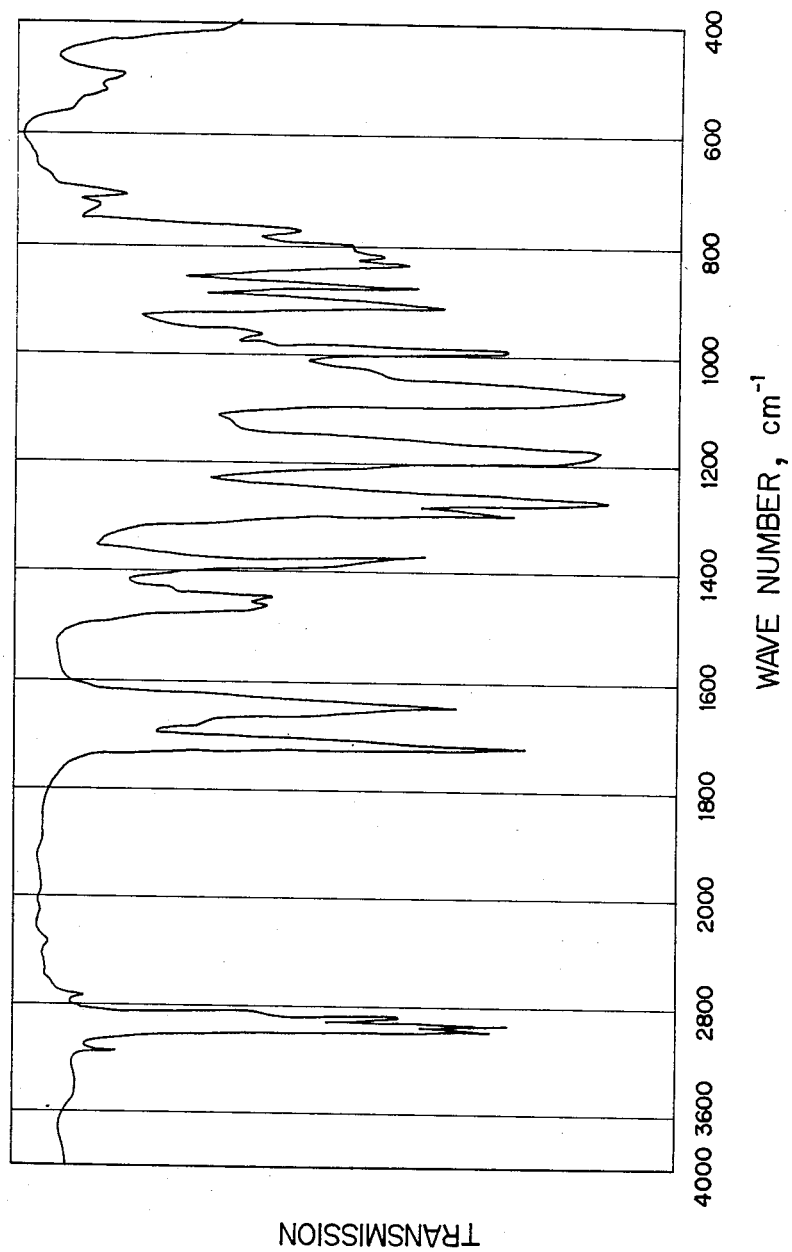

As is mentioned above, the novel organosilicon compound of the invention is represented by the general formula (I) and the symbol $R^1$ in the formula is a group selected from the class consisting of substituted and unsubstituted monovalent hydrocarbon groups including alkyl groups such as methyl, ethyl, propyl and butyl groups, alkenyl groups such as vinyl and allyl groups, aryl groups such as phenyl and tolyl groups and cycloalkyl groups such as cyclohexyl group as well as those substituted groups obtained by the replacement of a part or all of the hydrogen atoms in the above named hydrocarbon groups with substituent atoms or groups such as halogen atoms, cyano groups and the like exemplified by chloromethyl, 3,3,3-trifluoropropyl and cyano-methyl groups. The symbol R in the general formula (I) denotes a hydrogen atom or a group selected from the same class as in the case of $R^1$. The suffix m is a number of 2 or 3.

Particularly exemplary of the organosilicon compound in conformity with the above definition are the compounds expressed, denoting a methyl, an ethyl, a cyclohexyl, a n-propyl, a n-butyl, a phenyl and a glycidyl group by the symbols Me, Et, Ch, Pr, Bu, Ph and Gl, respectively, by the structural formulas of:

(A): $Me_2C=C(OMe)-O-SiMe(O-CMe=CH_2)_2$;
(B): $Et-CH=C(OMe)-O-SiMe(O-CMe=CH_2)_2$;
(C): $Me_2C=C(O-CH_2-CH_2-NMe_2)-O-SiMe(O-CMe=CH_2)_2$;
(D): $Me_2C=C(OCh)-O-SiMe(O-CMe=CH_2)_2$;
(E): $Me_2C=C(O-CH_2-CHEt-Bu)-O-SiMe(O-CMe=CH_2)_2$;
(F): $Me_2C=C(O-CH_2-CHEt-Bu)-O-Si(O-CMe=CH_2)_3$;
(G): $Me_2C=C(OMe)-O-SiMe(O-CEt=CH-Me)_2$;
(H): $Et-CH=C(OMe)-O-SiMe(O-CEt=CH-Me)_2$;
(J): $Me_2C=C(O-CH_2-CH_2-NMe_2)-O-Si(O-CMe=CH_2)_3$;
(K): $Pr.EtC=C(OCh)-O-SiMe(O-CMe=CH_2)_2$;
(L): $Ph-CH_2-CEt=C(O-CH_2-CHEt-Bu)-O-SiMe(O-CMe=CH_2)_2$;
(M): $Me_2C=C(OEt)-O-SiMe(O-CMe=CH_2)_2$;
(N): $Et-CH=C(OMe)-O-SiMe(O-CMe=CH_2)_2$;
(O): $Me_2C=C(OCh)-O-SiMe(O-CEt=CH_2)_2$;
(P): $Me_2C=C(O-CH_2-CH_2-NMe_2)-O-SiMe(O-CEt=CH_2)_2$;
(Q): $Et-CH=C(O-CH_2-CHEt-Bu)-O-SiMe(O-CMe=CH_2)_2$;
(R): $Me_2C=C(OGl)-O-SiMe(O-CMe=CH_2)_2$;
(S): $Et-CH=C(OMe)-O-Si(O-CMe=CH_2)_3$; and
(T): $Me_2C=C(OMe)-O-Si(O-CMe=CH_2)_3$.

None of the compounds expressed by the above given structural formulas is not described in any prior art publications. Each of these organosilicon compounds is highly hydrolyzable by virtue of the alkenyloxy groups bonded to the same silicon atom and reactive even at room temperature by a condensation reaction with the silanolic hydroxy groups in a hydroxy-terminated organopolysiloxane in the presence of the atmospheric moisture with liberation of an innoxious ketone compound so that the organopolysiloxane can be cross-linked to give a cured product. Thus, the novel organosilicon compound of the invention represented by the general formula (I) is useful as a curing agent in a RTV silicone composition.

The above described novel organosilicon compound or organosilane compound can readily be synthesized by the addition reaction between an α,β-unsaturated ester compound represented by the general formula (II) given above and an alkenyloxy-containing organosilane compound having a hyddrogen atom directly bonded to the silicon atom in a molecule as represented by the general formula (III) given above in the presence of a rhodium compound as a catalyst.

The α,β-unsaturated ester compound usable in the above mentioned addition reaction is exemplified by methyl crotonate, methyl acrylate and methacrylate, ethyl acrylate and methacrylate, propyl acrylate and methacrylate, butyl acrylate and methacrylate, pentyl acrylate and methacrylate, n-hexyl acrylate and methacrylate, cyclohexyl acrylate and methacrylate, 2-ethylhexyl acrylate and methacrylate, 2-(dimethylamino)ethyl acrylate and methacrylate, 2-(diethylamino)ethyl acrylate and methacrylate, and the like.

The alkenyloxy-containing organosilane compound of the general formula (III) is exemplified by those compounds expressed by the structural formulas of: $HSiMe(O-CMe=CH_2)_2$; $HSi(O-CMe=CH_2)_3$; $HSiMe(O-CEt=CH_2)_2$; and $HSi(O-CEt=CH_2)_3$, in which Me and Et each have the meaning as defined above. These silane compounds can readily be synthesized in a yield of 80 to 85% of the theoretical value by the reaction of a chlorosilane of the formula $HSi(R^1)_{3-m}Cl_m$ with a ketone compound such as acetone, methyl ethyl ketone, diethyl ketone and the like at an elevated temperature of, for example, 60° C.

The rhodium compound having activity for the addition reaction between them is exemplified by tris(triphenylphosphine) rhodium chloride of the formula $(PPh_3)_3RhCl$, tris(triphenylphosphine) rhodium iodide of the formula $(PPh_3)_3RhI$, tris(triphenylantimony) rhodium chloride of the formula $(SbPh_3)_3RhCl$, tris(tri-2-tolylphosphine) rhodium chloride of the formula $(P.2-Ty_3)_3RhCl$ and the like in which Ph is a phenyl group and 2-Ty is a 2-tolyl group. The addition reaction is performed by heating the reaction mixture containing the above mentioned rhodium catalyst at a temperature in the range from 60° to 120° C. or, preferably, from 70° to 90° C. to give the desired addition product in a yield of at least 95% of the theoretical value. This high yield of the alkenyloxy-containing organosilane compound advantageously ensures the outstandingly low production cost of the compound and, hence, the RTV silicone composition formulated therewith.

In the next place, a description is given on the RTV silicone composition of the invention formulated with the above described novel organosilicon compound as the curing agent. The base component, i.e. component (a), is a diorganopolysiloxane terminated at both molecular chain ends each with a silanolic hydroxy group. Such an organopolysiloxane compound is well known in the art of RTV silicone compositions and represented by the formula

$HO-SiR^1_2-O)_nH$, (V)

in which each $R^1$ is a substituted or unsubstituted monovalent hydrocarbon group as defined before for the general formula (I) and the suffix n is a positive integer to define the degree of polymerization of the diorganopolysiloxane. It is noted that the suffix n should have such a value that the viscosity of the diorganopolysiloxane is in the range from 100 to 1,000,000 centistokes or, preferably, from 1000 to 50,000 centistokes at 25° C. As is typically expresed by the above formula (V), the diorganopolsyiloxane has a straightly linear molecular structure although a small number of branches or a small degree of network formation may have no particularly adverse influences.

The component (b) which is blended with the component (a) and serves as a curing agent therefor is the organosilicon compound represented by the general formula (I) of which no detailed description is repeated here. The amount of the component (b) in the inventive RTV silicone composition should be in the range from 2 to 40 parts by weight or, preferably, from 3 to 20 parts by weight per 100 parts by weight of the component (a). When the amount of the component (b) is smaller than the above range, no sufficient density of the crosslinks can be formed in the composition as a matter of course. When the amount of the component (b) is in excess of the above range, on the other hand, the shrinkage of the composition in the course of curing would be excessively large and, in addition, the cured body of the composition may have a poor rubbery elasticity.

The curing accelerator as the component (c) in the inventive RTV silicone composition can be selected from a variety of compounds known in the art and used in various types of RTV silicone compositions including, for example, metal salts of carboxylic acids such as lead 2-ethylhexoate, dibutyltin diacetate, dibutyltin dilaurate, butyltin tri-2-ethylhexoate, iron 2-ethylhexoate, cobalt 2-ethylhexoate, manganese 2-ethylhexoate, zinc 2-ethylhexoate, tin (II) caprylate, tin naphthenate, tin oleate, tin butyrate, titanium naphthenate, zinc naphthenate, cobalt naphthenate, zinc stearate and the like, organic titanate esters such as tetrabutyl titanate, tetra-2-ethylhexyl titanate, triethanolamine titanate, tetra(isopropenyloxy) titanate and the like, organosiloxytitanium compounds, titanium $\beta$-carbonyl, aluminum alkoxides, amino-substituted alkoxysilane compounds such as 3-aminopropyl triethoxysilane, N-(3-trimethoxysilylpropyl) ethylenediamine and the like, amine compounds and salts thereof such as hexylamine, dodecylamine phosphate and the like, quaternary ammonium salts such as benzyl triethylammonium acetate and the like, alkali metal salts of lower fatty acids such as potassium acetate, sodium acetate, lithium oxalate and the like, hydroxylamine compounds such as dimethyl hydroxylamine, diethyl hydroxyamine and the like, and others. In particular, several kinds of the compounds having at least one tetrahydrocarbyl 2-guanidino group of the formula $(R_2N-)_2C=N-$, in which R is a monovalent hydrocarbon group such as methyl, ethyl and phenyl groups, in a molecule are preferred as the component (c) including those ompounds expressed by the following structural formulas, denoting a methyl, ethyl, propyl and phenyl group by the symbols Me, Et, Pr and Ph, respectively:

$(Me_2N-)_2C=NH;\quad (Me_2N-)_2C=N-CH_2-CH=CH_2;\ (Et_2N-)_2C=N-Me;$
$(Me_2N-)_2C=N-(-CH_2-)_3-Si(OMe)_3;$
$(Et.PrN-)(Et_2N-)C=N-(-CH_2-)_3-Si(OEt)_2-O-SiMe_3;$
$(Me_2N-)_2C=N-(-CH_2-)_3-Si(O-C-Me=CH_2)_3;$
$(Ph.MeN-)_2C=N-(-CH_2-)_3-O-(-CH_2-)_3-Si(-NMe.Et)_3;$
$Me-O-(-SiMe_2-O-)_{10}-SiMe[-(-CH_2-)_3-N=C(-NMe_2)_2]-O-Me;$
$(Me_2N-)_2C=N-(-CH_2-)_3-SiMe_3;$ and
$(Me_2N-)_2C=N-(-CH_2-)_3-Si(O-SiMe_3)_3.$ Among the above named 2-guanidino compounds, particularly preferable are the organosilicon compounds or a partial hydrolysis product thereof in view of the superior storability and stability of the composition formuulated therewith and the excellent properties, e.g. weathering resistance, heat resistance and the like, of the cured products obtained by curing the composition. It is of course that the above named curing accelerators can be used either singly or as a combination of two kinds or more according to need.

The amount of the curing accelerator as the component (c) in the inventive composition should be in the range from 0.01 to 10 parts by weight or, preferably, from 0.1 to 3 parts by weight per 100 parts by weight of the component (a). An amount of the curing accelerator smaller than the above range results in poor adhesion of the composition to the substrate surface on which it has been cured and low curability of the composition especially in the depth of a thick layer while a composition formulated with an excessively large amount of the curing accelerator has a poor stability in storage and gives a cured product having inferior properties.

The RTV silicone composition of the invention is obtained by merely blending the above described components (a), (b) and (c) uniformly in a dry atmosphere of air or nitrogen. It is of course optional that the components of the composition are stored in two separate packages, one containing a mixture of the components (a) and (b) and the other containing the component (c) or, alternatively, one containing the component (a) and the other containing a mixture of the components (b) and (c), and the contents of the two packages are blended together to form a completed composition directly before use.

It is also optional that the inventive composition is admixed with various kinds of known additives according to need, including fillers such as finely divided silica powder, silica aerogel, precipitated silica, diatomaceous earth, iron oxide, titanium dioxide, calcium carbonate, magnesium carbonate, zinc carbonate, asbestos, glass wool, carbon black, mica flakes and the like, pigments, dyes, aging retarders, antioxidants, antistatic agents, flame retardants, thermal conductivity improvers and others. The inventive room temperature curable composition can be prepared in the form of a paste or solution by diluting with a suitable organic solvent such as acetone, methyl ethyl ketone, hexane, octane, toluene, xylene and the like.

In the following, the preparation and characterization of the novel organosilicon compound of the invention and the RTV silicone composition formulated therewith are described in more detail by way of examples, in which the expression of "parts" always refers to "parts by weight".

EXAMPLE 1

Methyl di(isopropenyloxy)silane of the structural formula $HSiMe(OCMe=CH_2)_2$ was synthesized according to a known procedure by the reaction of acetone and methyl dichlorosilane followed by purification by distillation.

Into a glass flask equipped with a stirrer, reflux condenser, thermometer and dropping funnel were introduced 31.6 g (0.2 mole) of methyl di(isopropenyloxy)silane and 0.01 g of tris(triphenylphosphine) rhodium chloride as a catalyst to form a reaction mixture and 20.0 g (0.2 mole) of methyl methacrylate containing 0.01 g of di-tert-butyl hydroxytoluene as a polymerization inhibitor were added dropwise to the reaction mixture under agitation in the flask heated at 70° to 80° C. through the dropping funnel taking 30 minutes. The rate of the dropwise addition of the methyl methacrylate was controlled so that the temperature of the reaction mixture never exceeded 90° C. by the heat of reaction produced by the exothermic reaction. After completion of the addition of methyl methacrylate, the reaction mixture was further agitated for additional 30 minutes keeping the temperature at 80° to 90° C. to complete the reaction. The completion of the reaction was confirmed by the gas chromatographic analysis indicating disappearance of the starting reactants in the reaction mixture. Fractionating distillation of the thus obtained reaction mixture under reduced pressure gave 49.1 g of a fraction boiling at 92° to 93° C. under a pressure of 8 mmHg and having a refractive index $n_D^{25}$ of 1.4331, which was identified to be the organosilicon compound expressed by the formula (A) given before from the results of the gas chromatographic-mass spectrometric analysis and the infrared absorption spectroscopy to give the absorption spectrum of the compound illustrated in FIG. 1 of the accompanying drawing. The above mentioned yield of the product was 95.1% of the theoretical value.

EXAMPLES 2 to 5

The experimental procedure in each of these Examples was substantially the same as in Example 1 above excepting the replacement of the methyl methacrylate with an equimolar amount of one of the $\alpha,\beta$-unsaturated ester compounds indicated in Table 1 below. These product compounds obtained in Examples 2 to 5 were identified from the results of the gas chromatographic-mass spectrometric analysis and infrared absorption spectroscopy to be the organosilicon compounds expressed by the formulas (B), (C), (D) and (E) given before, respectively. FIGS. 2 to 5 illustrate the infrared absorption spectra of these compounds (B) to (E), respectively. Table 1 also includes the boiling point, refractive index $n_D^{25}$, yield of the product compound in g and in % of the theoretical value of each of the compounds.

TABLE 1

| | Example No. | | | |
|---|---|---|---|---|
| | 2 | 3 | 4 | 5 |
| $\alpha,\beta$-Unsaturated eater (taken, g) | Methyl crotonate (20.0) | Dimethylaminoethyl methacrylate (31.4) | Cyclohexyl methacrylate (23.8) | 2-Ethylhexyl methacrylate (39.6) |
| Boiling point, °C./mmHg | 96/8 | 130/9 | 127/5 | 122/3 |
| Refractive index | 1.4352 | 1.4444 | 1.4574 | 1.4462 |
| Yield, g | 49.6 | 61.1 | 53.1 | 69.2 |
| Yield, % | 96.2 | 96.9 | 95.8 | 97.2 |

EXAMPLE 6

An organopolysiloxane composition was prepared by uniformly blending 100 parts of a dimethylpolysiloxane terminated a both molecular chain ends each with a silanolic hydroxy group and having a viscosity of 20,000 centistokes at 25° C., 6 parts of the organosilicon compound expressed by the structural formula (L) given before and 0.5 part of a 2-guanidino-containing organosilicon compound 2-(3-trimethoxysilylpropyl) tetramethyl guanidine expressed by the formula (Me$_2$N—)$_2$C=N—C$_3$H$_6$—Si(OMe)$_3$ in a dry condition with exclusion of the atmospheric moisture. Almost no viscosity increase was noted in the course of blending.

The composition was shaped immediately after preparation by extrusion into a sheet of 2 mm thickness which was kept standing for 7 days in an atmosphere of 20° C. and 60% relative humidity so that a cured rubber sheet was obtained, of which the mechanical properties were determined according to the procedure specified in JIS K 6301 to give the results of the hardness 18 in the JIS scale, tensile strength of 8.5 kg/cm$^2$ and ultimate elongation at break of 220%.

The same test as above was repeated using the same composition kept in a hermetically sealed container for 6 months at 50° C. to find that the determination of the mechanical properties of the cured rubber sheet of 2 mm thickness prepared therefrom gave a hardness of 17 in the JIS scale, tensile strength of 8.8 kg/cm$^2$ and ultimate elongation at break of 230% indicating that this RTV silicone composition had excellent storability.

Further, the corrosiveness of the above prepared composition on metal surfaces was examined in the following manner. Thus, 50 g of the composition was introduced into a glass container of 150 ml capacity and a copper plate of 50 mm length, 25 mm width and 1 mm thickness was thrusted into the mass of the compisition to a depth of 20 mm from the lower end of the plate with the upper 30 mm length portion exposed and the container was tightly stoppered after addition of 2 g of water. After keeping in this condition for 7 days at 40° C., the copper plate was taken out of the organopolysiloxane composition and visually examined to find no noticeable changes on the surface indicating the absence of corrosiveness.

EXAMPLES 7 to 11

A base compound was prepared by uniformly blending 100 parts of a dimethylpolysiloxane terminated at both molecular chain ends each with a silanolic hydroxy group and having a viscosity of 5000 centistokes at 25° C., 20 parts of a dimethylpolysiloxane terminated at both molecular chain ends each with a trimethylsilyl group and having a viscosity of 50 centistokes at 25° C. and 12 parts of a surface-treated fumed silica filler.

In each of the Examples 7 to 11, 100 parts of the above prepared base compound were uniformly blended with 8 parts of the organosilicon oompound expressed by the structural formula (M), (N), (S) or (C) given before, respectively, as a curing agent and 0.5 part of 2-(3-trimethoxysilylpropyl) tetramethyl guanidine (Examples 7 to 10) or a combination of 0.4 part of the same guanidine compound and 0.1 part of dibutyltin diacetate (Example 11) as a curing accelerator to give a RTV silicone composition.

Each of the thus prepared RTV silicone compositions, either as prepared or after storage for 6 months at 50° C. in a hermetically sealed condition, was shaped and cured into a rubber sheet of 2 mm thickness in the same manner as in Example 6 and the mechanical properties were determined to give the results shown in Table 2 below.

TABLE 2

| | | Example No. | | | | |
|---|---|---|---|---|---|---|
| | | 7 | 8 | 9 | 10 | 11 |
| As prepared | Hardness, JIS | 28 | 27 | 32 | 26 | 30 |
| | Tensile strength, kg/cm$^2$ | 18 | 16 | 24 | 16 | 18 |
| | Ultimate elongation, % | 380 | 400 | 260 | 410 | 320 |
| After 6 months at 50° C. | Hardness, JIS | 25 | 27 | 31 | 24 | 27 |
| | Tensile strength, kg/cm$^2$ | 15 | 14 | 23 | 16 | 12 |
| | Ultimate elongation, % | 350 | 380 | 250 | 430 | 260 |

What is claimed is:

1. An organosilane compound represented by the general structural formula $$R_2CH-CR=C(OR)-O-Si(R^1)_{3-m}(O-CR=CH-R)_m,$$

in which each R is a hydrogen atom or a substituted or unsubstituted monovalent hydrocarbon group independently from the others, $R^1$, if any, is a substituted or unsubstituted monovalent hydrocarbon group and the suffix m is 2 or 3.

2. An organosilicon compound expressed by the structural formula $$Me_2C=C(OMe)-O-SiMe(O-CMe=CH_2)_2,$$

in which Me is a methyl group.

3. An organosilicon compound expressed by the structural formula $$Et-CH=C(OMe)-O-SiMe(O-CMe=CH_2)_2,$$

in which Me is a methyl group and Et is an ethyl group.

4. An organosilicon compound expressed by the structural formula $$Me_2C=C(O-CH_2-CH_2-NMe_2)-O-SiMe(O-CMe=CH_2)_2,$$

in which Me is a methyl group.

5. An organosilicon compound expressed by the structural formula $$Me_2C=C(OCh)-O-SiMe(O-CMe=CH_2)_2,$$

in which Me is a methyl group and Ch is a cyclohexyl group.

6. An organosilicon compound expressed by the structural formula $$Me_2C=C(O-CH_2-CHEt-Bu)-O-SiMe(O-CMe=CH_2)_2,$$

in which Me is a methyl group, Et is an ethyl group and Bu is a n-butyl group.

7. A method for the preparation of an organosilane compound represented by the general structural formula $$R_2CH-CR=C(OR)-O-Si(R^1)_{3-m}(O-CR=CH-R)_m,$$

in which each R is a hydrogen atom or a substituted or unsubstituted monovalent hydrocarbon group independently from the others, $R^1$, if any, is a substituted or unsubstituted monovalent hydrocarbon group and the suffix m is 2 or 3, which comprises reacting an $\alpha,\beta$-unsaturated ester compound represented by the general formula $$R_2C=CR-CO-OR,$$

in which each R is a hydrogen atom or a substituted or unsubstituted monovalent hydrocarbon group independently from the others, and an alkenyloxy-containing silane compound represented by the general formula $$HSi(R^1)_{3-m}(O-CR=CH-R)_m,$$

in which R has the meaning as defined above, $R^1$, if any, is a substituted or unsubstituted monovalent hydrocarbon group and the suffix m is 2 or 3, in the presence of a rhodium compound as a catalyst.

8. The method as claimed in claim 7 wherein the rhodium compound as the catalyst is selected from the class consisting of tris(triphenylphosphine) rhodium chloride of the formula $(PPh_3)_3RhCl$, tris(triphenylphosphine) rhodium iodide of the formula $(PPh_3)_3RhI$, tris(triphenylantimony) rhodium chloride of the formula $(SbPh_3)_3RhCl$ and tris(tri-2-tolylphosphine) rhodium chloride of the formula $(P.2-Ty_3)_3RhCl$, the symbols Ph and 2-Ty each denoting a phenyl group and a 2-tolyl group, respectively.

9. The method as claimed in claim 7 wherein the reaction is performed at a temperature in the range from 60° to 120° C.

* * * * *